(12) United States Patent
Merkus

(10) Patent No.: US 9,402,811 B2
(45) Date of Patent: Aug. 2, 2016

(54) OROMUCOSAL LIQUID ESTRADIOL COMPOSITIONS

(71) Applicant: INNOTESTO BVBA, Kasterlee (BE)

(72) Inventor: Franciscus Wilhelmus Henricus Maria Merkus, Kasterlee (BE)

(73) Assignee: INNOTESTO BVBA, Kasterlee (BE)

( * ) Notice: Subject to any disclaimer, the term of this patent is extended or adjusted under 35 U.S.C. 154(b) by 0 days.

(21) Appl. No.: 14/370,435

(22) PCT Filed: Jan. 4, 2013

(86) PCT No.: PCT/EP2013/050110
§ 371 (c)(1),
(2) Date: Jul. 2, 2014

(87) PCT Pub. No.: WO2013/102665
PCT Pub. Date: Jul. 11, 2013

(65) Prior Publication Data
US 2014/0371191 A1 Dec. 18, 2014

(30) Foreign Application Priority Data
Jan. 4, 2012 (GB) .................................. 1200062.6

(51) Int. Cl.
| | | |
|---|---|---|
| A61K 31/56 | (2006.01) | |
| A61K 9/00 | (2006.01) | |
| A61K 9/08 | (2006.01) | |
| A61K 31/565 | (2006.01) | |
| A61K 47/10 | (2006.01) | |
| A61K 47/14 | (2006.01) | |

(52) U.S. Cl.
CPC . *A61K 9/006* (2013.01); *A61K 9/08* (2013.01); *A61K 31/565* (2013.01); *A61K 47/10* (2013.01); *A61K 47/14* (2013.01)

(58) Field of Classification Search
None
See application file for complete search history.

(56) References Cited

U.S. PATENT DOCUMENTS

| | | | |
|---|---|---|---|
| 5,766,620 A * | 6/1998 | Heiber et al. .................. | 424/436 |
| 6,110,486 A * | 8/2000 | Dugger, III ................... | 424/435 |
| 8,647,665 B2 * | 2/2014 | Simes et al. ................... | 424/449 |
| 2003/0077229 A1 | 4/2003 | Dugger | |
| 2007/0219171 A1 * | 9/2007 | Lulla et al. .................... | 514/177 |

FOREIGN PATENT DOCUMENTS

| | | |
|---|---|---|
| JP | H06321771 A | 11/1994 |
| WO | WO-97/38662 A2 | 10/1997 |
| WO | WO-2005/041943 A1 | 5/2005 |
| WO | WO-2005049026 A1 | 6/2005 |
| WO | WO-2009036355 A1 | 3/2009 |
| WO | WO-2010/089078 A1 | 8/2010 |

OTHER PUBLICATIONS

Hassan et al., "Chemical permeation enhancers for transbuccal drug delivery," Expert Opon Drug Deliv Jan. 2010;7(1):97-112 (Abstract).*
Database Biosis [Online] Biosciences Information Service, Philadelphia, PA, US; 1995, Goldberg-Cettina Melinda et al: "Enhanced transdermal delivery of estradiol in vitro using binary vehicles of isopropyl myristate and short-chain alkanols", XP009167205, Database accession No. PREV199598097252 abstract & International Journal of Pharmaceutics (Amsterdam), vol. 114, No. 2, 1995, pp. 237-245, ISSN: 0378-5173.
Database Biosis [Online] Biosciences Information Service, Philadelphia, PA, US; Nov. 15, 1998, Kitano Manabu et al: "Buccal absorption through golden hambster cheek pouch in vitro and in vivo of 17beta-estradiol from hydrogels containing three types of absorption enhancers", XP009167375, Database accession No. PREV199900000654 absract & International Journal of Pharmaceutics (Amsterdam), vol. 174, No. 1-2, Nov. 15, 1998, pp. 19-28, ISSN: 0378-5173.
International Search Report of PCT/EP2013/050110 filed Jan. 4, 2013.
Liu et al. "Effects of Isopropanol-Isopropyl Myristate Binary Enhancers on In Vitro Transport of Estradiol in Human Epidermis: A Mechanistic Evaluation." *J. Pharma. Sci.* 98.2(2009):565-572.

* cited by examiner

*Primary Examiner* — Jared D Barsky
(74) *Attorney, Agent, or Firm* — Mintz Levin Cohn Ferris Glovsky and Popeo, P.C.; Muriel Liberto, Esq.

(57) ABSTRACT

The present invention relates to low dose estradiol solutions for oromucosal administration suitable in replacement therapy or suppletion of low estradiol levels and also for preventing, alleviating or treating symptoms associated with low endogenous levels of estradiol in female subjects.

8 Claims, No Drawings

OROMUCOSAL LIQUID ESTRADIOL COMPOSITIONS

RELATED APPLICATION

This application is a national stage application filed under 35 U.S.C. 371, of International Application No. PCT/EP2013/050110, filed Jan. 4, 2013, which claims priority to GB 1200062.6 filed Jan. 4, 2012, the contents of which are hereby fully incorporated by reference.

The present invention relates to low dose estradiol solutions for oromucosal administration suitable in replacement therapy or suppletion of low estradiol levels and also for preventing, alleviating or treating symptoms associated with low endogenous levels of estradiol in female subjects.

BACKGROUND OF THE INVENTION

Current estradiol therapy includes oral, transdermal, injectable and vaginal formulations. Transdermal delivery comprises patches, gels, lotions and sprays, while vaginal products include suppositories, creams, and rings.

Estradiol, when taken orally as tablets, pills or capsules, is converted for a large part to estrone after absorption in the gastrointestinal tract and metabolism in the liver (first-pass metabolism). This causes an imbalance in the estradiol/estrone ratio, which is normally 1:1 in premenstrual women. This imbalance is mainly responsible for a change in lipids and clotting factors. Non-oral products (transdermal, vaginal) avoid this hepatic first-pass metabolism and therefore are considered first choice in estradiol suppletion.

In general, it is advisable to use the lowest dose of the hormone estradiol possible, because overdosing may lead to side effects related to unphysiological hormone levels. Low-dose non-oral products are first choice because of (1) the low-dose administered, (2) the physiological ratio between levels of estradiol and its metabolite estrone, and (3) as a consequence the decreased risk of adverse effects. The use of very low doses may also be beneficial as opposed treatment (continuous or cyclic co-administration of a progestogen) is not an absolute requirement because the endometrium does not proliferate upon administration of very low doses of estradiol.

In the research into new estradiol products, non-oral administration has been considered, including products for nasal and oromucosal administration. U.S. Pat. No. 5,955,098 discloses a buccal aerosol spray, comprising a propellant 50-95%, a non-polar solvent 5-50%, the active drug compound 0.001-15% (including estradiol), and a flavoring agent 0.05-5%. U.S. Pat. No. 6,110,486 discloses a buccal spray containing estradiol, dissolved in a pharmacologically acceptable polar solvent, comprising in weight % of total composition: polar solvent 75-99.8%, active compound 0.68-40%. As solvents for the sprays there are used low molecular weight polyethylene glycols (PEG) of 200-1000 MW (preferably 200-600) and also low molecular weight alcohols and polyols, such as glycerin and water. Illustrated is a spray formulation containing estradiol and 85% polyethylene glycol. However, this solvent has a bitter, burning taste in the mouth, making a spray, based mainly on such an ingredient, poorly acceptable for chronic use.

US 2011/0097405 discloses an oromucosal estradiol product, which is absorbed mainly in the oral cavity and not in the gastro-intestinal tract. It is a water-soluble film, called wafer. Such wafers containing estradiol in a low dose dissolve quickly in the mouth, thereby releasing estradiol, which then can be absorbed via the oromucosal route. Buccal tablets comprising estradiol are disclosed in EP 0 371 466 and WO 2010/089078. Medicated papers for oromucosal administration containing estradiol and a cyclodextrin are described in EP 1 867 321.

Formulations of dimethyl-$\beta$-cyclodextrin complexes of 17$\beta$-estradiol and/or progesterone in an aqueous solution for nasal application have been described in EP 0349091. One such formulation containing 17$\beta$-estradiol complexed in methylated-$\beta$-cyclodextrin has been authorized for medical use under the trade name Aerodiol™. This nasal spray product, administered in a low dose of 300 µg/day, was as effective as a 2 mg oral tablet/day in treating menopausal symptoms. It showed reduced adverse effects, i.e. fewer incidences of mastalgia and withdrawal bleedings. Furthermore, beneficial effects on some lipid parameters, on markers of bone resorption, bone formation and bone mineral density were reported. Finally, less breast tenderness was found with intranasal administration of estradiol as compared to oral treatment.

Because of the side effects of frequent nasal administration, Aerodiol™ is recommended for once daily administration in a high dose resulting in high peak estradiol levels. These are reached within 10-30 min. and the levels return to 10% of the peak value in about two hours after administration (Devissaguet et al., Eur. J. Drug Metabol. Pharmacokinetics 1999; 24: 265-271). This means that once daily intranasal administration of Aerodiol™ results in a "pulsatile" profile, comprising one large peak per day, followed by a period during which estradiol levels remain at a low level. Peak levels after administration of 300 µg estradiol by the required quantity of Aerodiol™ nasal spray reach values of 1400 pg/l. Normal estradiol levels differ slightly per laboratory, but range from 100-500 pg/ml during a menstrual cycle. This means that the peak level of 1400 pg/ml, obtained with nasal Aerodiol™, is about 3 times higher than the highest normal levels in premenopausal women.

A further disadvantage related to nasal administration is that the access to the nasal mucosa can be compromised in instances such as common cold or allergy resulting in a running or blocked nose. This results in inconsistent or even no nasal absorption. The product characteristics of Aerodiol™ teach that in that instance the patient, should administer a double dose of Aerodiol™ via the oromucosal route to reach similar estradiol serum levels.

Moreover, nasal administration may give rise to local side effects in the nose, such as local irritation, itching, rhinorrhoea, sneezing and nosebleeds. Multiple nasal administrations increase these undesired side effects.

It is a first object of the invention to avoid nasal administration of estradiol and the side effects associated therewith.

It is a second object of the invention to provide an estradiol composition for oromucosal administration that does not require the administration of high doses of estradiol, such as for example the double dose required for oromucosal administration of Aerodiol™.

Further, it is an object of the invention to provide a new dosage regimen for estradiol administration that provides a physiological pharmacokinetic profile approaching normal estradiol plasma levels. A particular object is the provision of a dosage regimen with low estradiol peak levels, in particular a regimen that keeps the highest estradiol levels under 500 pg/ml, and avoids the high peak serum levels seen with the administration of existing nasal formulations.

It is also an object of the invention to provide a new and improved dosage form comprising a low dose estradiol formulation, for application to the oral mucosa, that (1) delivers a similar or better bioavailability than nasal administration, (2) provides a dosage form whereby the dose can be individualized, (3) with a flexible dosage frequency and (4) offers better patient compliance.

SUMMARY OF THE INVENTION

In one aspect, the present invention relates to a non-aqueous (or substantially non-aqueous) solution containing 0.01-0.9% (w/v) of estradiol, or an equivalent amount of a pharmaceutically acceptable hydrate or ester thereof, 5-30% (v/v) of a $C_2$-$C_5$ alcohol and 70-95% (v/v) of an ester of a $C_2$-$C_6$ alcohol and a $C_8$-$C_{22}$ fatty acid for use in the treatment of a human female with decreased estradiol levels by oromucosal administration of a dose of said solution, said dose containing 0.01-0.3 mg of estradiol, or an equivalent amount of a pharmaceutically acceptable hydrate or an ester thereof.

In another aspect, the present invention relates to a solution containing 0.01-0.9% (w/v) of estradiol, or an equivalent amount of a pharmaceutically acceptable hydrate or ester thereof, 5-30% (v/v) of a $C_2$-$C_5$ alcohol and 70-95% (v/v) of an ester of a $C_2$-$C_6$ alcohol and a $C_8$-$C_{22}$ fatty acid for use in the manufacture of a medicament for the treatment of a human female with reduced estradiol levels by oromucosal administration of a dose of said solution, said dose containing 0.01-0.3 mg of estradiol, or an equivalent amount of a pharmaceutically acceptable hydrate or ester thereof.

The solutions of the invention may be administered in a predetermined quantity by a number of administrations, either at one point in time or at more points in time, selected such that the resulting estradiol blood serum levels mimic the normal levels throughout the day. Suitably, the solutions of the invention may be administered in such a manner as to restore the female's estradiol serum levels to normal values.

In accordance with these aspects of the invention, therefore the dose may be administered by single or multiple administrations as described below. The dose may have a volume of 10 μl to 300 μl of said solution, preferably 25 μl to 100 μl—for example 25 μl, 50 μl or 100 μl.

The human female may be treated with a dose of said solution at one or more points in time. The solutions of the invention may be administered once daily or multiple times daily, for example two, three, four, five or six doses per day. In some embodiments, multiple administrations may be given at regular periods of time, e.g. every hour or every two, three, or four hours.

In one embodiment, the dose may be administered intermittently in a time period that is in the range of 1 to 4 hours, in particular at equal time intervals, for example at intervals of about 1, or 2, or 3, or of 4 hours.

Typically, the solutions may be administered by 1-6 doses per day, for example 1, 2, 3, 4, 5 or 6 doses per day, or by 1-4 doses per day, or by 1-2 doses per day.

In a different aspect, the present invention relates to a method of treatment of a human female with reduced estradiol levels, said method comprising administering oromucosally to a human female patient in need thereof, at one or more points in time, a dose of a solution containing 0.01-0.9 (w/v) of estradiol, or an equivalent amount of a pharmaceutically acceptable hydrate or ester thereof, 5-30% (v/v) of a $C_2$-$C_5$ alcohol and 70-95% (v/v) of an ester of a $C_2$-$C_6$ alcohol and a $C_8$-$C_{22}$ fatty acid; wherein said dose is given by single or multiple administration and comprises 0.01-0.3 mg of estradiol, or an equivalent amount of a pharmaceutically acceptable hydrate or ester thereof.

The dose may have a volume of 10 μl to 300 μl of said solution, preferably 25 μl to 100 μl—for example 25 μl, 50 μl or 100 μl.

The oromucosal administration can be by a spray, a dosage pen or a device delivering drops. Thus in a further aspect, the invention provides a dosage form comprising a spray, a dosage pen or a device delivering drops containing the solution as specified herein.

The estradiol solutions of the invention can be used in a dosage regimen that can be individually adapted by one or more of the following: 1. by the dose as such, 2. the volume of the sprays or drops, 3. the number of sprays or drops, 4. by a single or multiple administration, 5. at one or more points in time, and 6. by the frequency of the daily administrations. The solution may be administered according to the regimens described above.

In one embodiment, the solutions of the invention or for use in the invention contain 10-30% ethanol (v/v), 70-90% of isopropyl myristate or isopropyl palmitate and 0.01-0.9% estradiol, or an equivalent amount of a pharmaceutically acceptable hydrate or ester thereof.

In one embodiment, the solutions of the invention or for use in the invention contain 0.01-0.5% (w/v) estradiol or an equivalent amount of a pharmaceutically acceptable hydrate or ester thereof.

In yet another aspect, the present invention relates to a solution comprising estradiol, or an equivalent amount of a pharmaceutically acceptable hydrate or ester thereof, as specified herein, for the treatment, prevention or relief, or for use in the manufacture of a medicament for use in the treatment, prevention or relief, of symptoms in a human female caused by insufficient endogenous production of estrogen. Examples of these symptoms include headaches, nausea, vasomotor symptoms (hot flushes), symptoms of urogenital atrophy, decrease in bone mineral density, osteoporosis and increased risk or incidence of bone fractures.

In yet another aspect, the present invention relates to a method of treating, preventing or relieving symptoms in a human female caused by insufficient endogenous production of estrogen, said method comprising the oromucosal administration of a solution comprising estradiol or an equivalent amount of a pharmaceutically acceptable hydrate or ester thereof, as specified herein. Examples of these symptoms are as cited above.

In yet another aspect of the present invention, there is provided a solution of estradiol, as specified herein, for use in the treatment or manufacture of a medicament for use in the treatment of decreased estradiol levels in a human female by administration at one or more points in time via the oromucosal route of a predetermined quantity of said solution by a single or multiple administration, said predetermined quantity representing a dose of 0.01-0.3 mg of estradiol, in a volume in the range of 10 μl to 300 μl, preferably 25 μl to 100 μl—for example 25 μl, 50 μl or 100 μl. Administration of estradiol in this manner has been found to cause a controlled increase of estradiol serum levels that is proportional to the amount of estradiol administered.

In yet another aspect of the invention, there is provided a non-aqueous (or substantially non-aqueous) solution containing 0.01-0.9% (w/v) of estradiol, or an equivalent amount of a pharmaceutically acceptable hydrate or ester thereof, 5-30% (v/v) of a $C_2$-$C_5$ alcohol and 70-95% (v/v) of an ester of a $C_2$-$C_6$ alcohol and a $C_8$-$C_{22}$ fatty acid for use in the treatment of a human female with hot flushes; wherein said solution is administered by oromucosal, preferably buccal, buccomaxillary or buccogingival, administration as soon as the hot flushes occur at a dosage of 0.01-0.3 mg estradiol in a volume of said solution in the range 10-300 μl, preferably 25 μl to 100 μl; for example 25 μl, 50 μl or 100 μl.

In yet another aspect of the invention there is provided a solution of estradiol, as specified herein, for use in the treatment or manufacture of a medicament for use in the treatment of decreased estradiol levels in a postmenopausal human female by administration at one or more points in time via the oromucosal route of a predetermined quantity of said solution by a single or multiple administration; said predetermined quantity representing a dose of 0.01-0.3 mg of estradiol, thereby to elevate and/or keep the estradiol level in the female higher than 20, higher than 30, higher than 40 or higher than 50 pg/ml, and lower than 500 pg/ml, especially between 50-500 pg/ml, during a required period of time.

In yet another aspect, the present invention relates to a non-aqueous (or substantially non-aqueous) solution containing 0.01-0.9% (w/v) of estradiol, or an equivalent amount of a pharmaceutically acceptable hydrate or ester thereof, 5-30% (v/v) of a $C_2$-$C_5$ alcohol and 70-90% (v/v) of an ester of a $C_2$-$C_6$ alcohol and a $C_8$-$C_{22}$ fatty acid.

In some embodiments, the $C_2$-$C_5$ alcohol may be ethanol and the ester of a $C_2$-$C_6$ alcohol and a $C_8$-$C_{22}$ fatty acid may be isopropyl myristate or isopropyl palmitate.

DETAILED DESCRIPTION OF THE INVENTION

Any reference cited herein is hereby incorporated by reference.

As used herein, the term "subject" refers to a human being. The terms "subject" and "patient" are used interchangeably.

The terms "level", "serum level", "blood level", "plasma level" and "blood serum level" are used herein interchangeably.

As used herein, the term "oromucosal" refers to buccal, buccomaxillary sublingual, gingival, buccogingival and palatal.

The term "solutions" refers to solutions that are liquid at ambient and body temperature.

When used herein, the term "estradiol" means 17-alpha-estradiol or 17-beta-estradiol. Preferred in the present invention is estradiol is in the form of 17-beta-estradiol. The terms "estradiol" and "estradiol derivatives" are intended to cover estradiol itself as well as any pharmaceutically acceptable hydrates, esters or derivatives thereof. The term "pharmaceutically acceptable esters of estradiol" refers to esters of estradiol such as, for example, estradiol valerate, estradiol acetate, estradiol phenylpropionate, estradiol propionate, estradiol enanthate, estradiol undecylate, estradiol benzoate, estradiol cypionate, estradiol sulfate and estradiol sulfamate.

The term "$C_2$-$C_5$ alcohol" refers to alcohols having from two to five carbon atoms, e.g. 2, 3, 4 or 5 carbon atoms. Particular subgroups of these are the monohydric saturated branched or non-branched $C_2$-$C_5$ alcohols such as for example ethanol, 1-propanol, isopropanol, butanol, pentanol or the dihydric alcohols such as propylene glycol, or trihydric alcohols such as glycerol.

The phrase "pharmaceutically acceptable esters of $C_8$-$C_{22}$ fatty acids and $C_2$-$C_6$ alcohols" refers to such esters and also includes vegetable oils. $C_8$-$C_{22}$ fatty acids comprise fatty acids having from 8 to 22 carbon atoms (e.g. 8, 10, 12, 14, 16, 18, 20 or 22 carbon atoms) such as, e.g. myristic acid, palmitic acid, stearic acid, arachidic acid or oleic acid. $C_2$-$C_6$ alcohols comprise alcohols having from 2 to 6 carbon atoms (.e.g. 2, 3, 4, 5 or 6 carbon atoms), in particular the $C_2$-$C_5$-alcohols as specified herein, as well as the homologs with 6 carbon atoms such as hexanol, also including diols and triols, such as ethanol, isopropanol, propylene glycol, and glycerol.

Examples of esters of $C_8$-$C_{22}$ fatty acids and $C_2$-$C_6$ alcohols include isopropyl myristate, isopropyl palmitate and iso-propyl stearate. Examples of vegetable oils are sesame oil, corn oil, castor oil and olive oil.

The term "non-aqueous (or substantially non-aqueous)" as used herein means that the solution does not contain water, or only a small amount of water, such as less than 5%, or less than 3%, or less than 1%.

The term "v/v" refers to volume per volume, and "w/v" to weight per volume.

The term "about", when used in relation to a numerical value, has the meaning generally understood in the relevant art. In certain embodiments the term "about" may be left out or may be interpreted to mean the numerical value ±10%; or ±5%; or ±2%; or ±1%.

The present invention solution is administered oromucosally. This means the solution in a specific dose or volume is administered to the oral cavity and the active drug substance is subsequently absorbed via one or more of the oromucosal (lingual, sublingual, buccal, gingival, and palatal) membranes.

The solutions of the invention may be conveniently self-administered by the patient or administered by a physician, carer or nurse.

The solutions may be administered in a single or multiple administration, meaning that a certain dose amount of estradiol is administered all at once or in one or more sub-doses. For example, one puff of a spray solution may be administered, representing the full desired dose, or one, two or more puffs of a smaller dose may be administered, preferably shortly after one another.

In particular embodiments of this invention, the solutions contain from 0.01-0.9% (w/v), or from 0.05-0.8% (w/v), or from 0.1-0.7% (w/v), or from 0.2-0.6% (w/v), or from 0.3-0.5% (w/v), or from 0.1-0.4% (w/v), or from 0.1-0.3% (w/v) of estradiol or an equivalent amount of a pharmaceutically acceptable hydrate or ester thereof.

The quantity of estradiol to be administered typically may be determined after measuring the estradiol serum concentrations. Depending on the results of these measurements, the physician can decide to prescribe an estradiol solution of lower or higher concentration and/or the dosing regimen can be individually adapted by either the dose as such, or the volume of the administrations, or the number of administrations, or the frequency of daily administrations.

In particular embodiments of this invention, the solution contains from 5-30% (v/v), or from 10-30% (v/v), or from 5-25% (v/v), or from 10-25% (v/v), or from 15-25% (v/v) of the $C_2$-$C_5$ alcohol, preferably ethanol.

In the solutions of the present invention containing ethanol, when present in a concentration of at least 10% (v/v), the ethanol not only acts as solvent, but also as an effective antimicrobial preservative. This is advantageous because it makes the use of and inclusion of other preservatives in such solutions superfluous.

In one embodiment the solutions contain from 5-40% (v/v), or from 5-35% (v/v) of the $C_2$-$C_5$ alcohol. Solutions with ethanol concentrations exceeding 30% (v/v) may cause irritation or other side effects, but these can be alleviated by adding certain ingredients.

In particular embodiments of this invention, the solution contains from 70-95% (v/v) of an ester of a $C_{2-6}$ alcohol and a $C_{8-22}$ fatty acid, or from 75-90% or from 80-8% of such esters.

As mentioned above, the solutions of the invention may be administered in a predetermined quantity by a number of administrations, either at one point in time or at more points in time, selected such that the resulting estradiol blood serum levels mimic the normal levels throughout the day. Thus, the solutions of the invention may be administered in a predetermined quantity and by a number of administrations, either at one point in time or at more points in time, to increase the estradiol serum levels to normal values, in particular to levels that are higher than 20 pg/ml, or serum levels that are in the range of 10-500 pg/ml, 50-100 pg/ml, or 100-500 pg/ml. In one embodiment said serum levels are maintained for more than 3 hours, preferably maintained at a level of higher than 20 pg/ml for 3 hours.

The solutions of the invention may be administered once daily or multiple times daily, for example two, three, four, five or six times per day. In particular, multiple administrations may be given at regular periods of time, e.g. every hour or every two, three, or four hours.

In one embodiment, the dose may be administered intermittently in a time period that is in the range of 1 to 4 hours, in particular at equal time intervals, for example at intervals of about 1, or 2, or 3, or of 4 hours.

The solution may be administered by 1-6 administrations per day, for example 1, 2, 3, 4, 5 or 6 administrations per day, or by 1-4 per day administrations, or by 1-2 administrations per day.

The solutions of the invention may be administered in various ways, for instance by a spray or as drops. Devices that can be used are (sterile or non-sterile) multi-dose or unit-dose containers or multi-dose or unit-dose sprays or drop devices or any other container or pen from which a specific volume of e.g. 25 µl, 50 µl etc. can be transferred to the oral cavity. Devices to administer the estradiol solutions of the invention include glass bottles with a spray device, but any other device (with or without the use of propellants) for administration of volumes in the range of 25 µl to 120 µl, e.g. 25 µl, 50 µl, 70 µl, 90 µl, 100 µl, or 120 µl. When using a spray, any kind of device known in the art having a capacity in the range of about 25-200 µl per dose (or puff), e.g., about 50, 75, 100, 125, 150, 175 µl. Also drop dispensers or dosage pens may be suitable to administer the solutions to the oral cavity of the patient.

In certain embodiments, the present invention solution comprises per dosage volume, administered for example per drops, dosage pen, or spray, a dose of estradiol in the range of 10-300 µg of estradiol, such as 25-300 µg of estradiol, e.g. 50-300 µg of estradiol. Typically the dose per dose comprises 10-200 µg of estradiol, such as 10-100 µg of estradiol or 25-100 µg of estradiol. As a daily dose total amounts of 100-600 µg of estradiol, preferably 100-300 µg of estradiol may be administered.

This invention also relates to the use of a solution of estradiol, as specified herein, in the treatment of decreased estradiol levels in a female by oromucosal administration of a predetermined quantity of said solution, causing a controlled increase of the estradiol blood serum levels that is proportional to the amount of estradiol administered.

The controlled increase of estradiol serum levels may be between about 150-300 pg/ml for each 0.05 mg of estradiol administered, or between about 75-150 pg/ml for each 0.025 mg of estradiol administered.

The dosing regimen with the estradiol solutions of this invention may avoid the administration of large doses thereby causing a peak level of estradiol, well above normal levels. The present dosing regimen avoids the local side effects associated with frequent nasal administrations, such as local irritation, itching, rhinorrhoea, sneezing and nosebleeds. In addition, with the solutions of this invention lower doses can be administered as compared with aqueous cyclodextrin formulations of estradiol, in particular the Aerodiol™ formulation.

The dosage regimen for estradiol administration of the invention provides a physiological pharmacokinetic profile close to normal estradiol plasma levels. The dosage regimen of the invention moreover shows lower estradiol peak levels, while keeping the highest estradiol levels under 500 pg/ml, and avoids the high peak serum levels seen with the administration of nasal formulations.

The present estradiol dose regimen (1) delivers a similar or better bioavailability than nasal administration, (2) provides a dosage form whereby the dose can be individualized, (3) with a flexible dosage frequency, and (4) offers better patient compliance.

In another embodiment, the solutions of the invention comprise a further active drug substance, such as progesterone or another progestogen compound, for example in a range of 0.1-5% (w/v), 0.5-4% (w/v), 1-3% (w/v/) or 1.5%-2.5% (w/v).

In some embodiments, the solvent in the solutions of the invention may consist or consist essentially of 5-30% (v/v) of a $C_2$-$C_5$ alcohol and 70-90% (v/v) of an ester of a $C_2$-$C_6$ alcohol and a $C_8$-$C_{22}$ fatty acid. In other embodiments, the solutions of the invention the solvent may consist or consist essentially of 0.01-0.9% (w/v) of estradiol or an equivalent amount of a pharmaceutically acceptable hydrate or ester thereof, 5-30% (v/v) of a $C_2$-$C_5$ alcohol and 70-90% (v/v) of an ester of a $C_2$-$C_6$ alcohol and a $C_8$-$C_{22}$ fatty acid.

In addition, the solutions of the invention may also include a sweetener or flavoring agent, for example in a concentration of 1-5% (w/v), Examples of sweeteners or flavoring agents can be found in the pharmaceutical literature. For instance saccharin can be added to the solutions. Any of the ingredients to be added preferably are in the list of GRAS (generally regarding as being safe) list of chemicals used in pharmaceutical preparations and those that are currently allowed in topical and parenteral formulations.

In other embodiments the present invention solution may contain also antioxidants, viscosity enhancers, viscosity modulators, surfactants and excipients regulating the adherence of the solution the mucous membranes in the oral cavity. All those excipients are known from the pharmaceutical literature (for instance Remington: The Science and Practice of Pharmacy, 21th edition, PA Lippincott Williams & Wilkins, 2005).

A propellant may be added where the solution is adapted for delivery in spray form. Suitable propellants include hydrogen-containing chlorofluorocarbons, hydrogen-containing fluorocarbons such as heptafluoroethane, dimethylfluoropropane, tetrafluoropropane, butane, isobutane, dimethyl ether, diethyl ether and any other non-CFC and CFC propellants. A preferred propellant is 1,1,1,2-tetrafluoroethane (HFA 134a).

The present invention relates to a solution of estradiol for use in the treatment of decreased estradiol levels in a female subject by administration via the oromucosal route of a predetermined quantity of said solution, by a single or multiple administration, at one or more points in time, said quantity representing a dose of 0.01-0.3 mg of estradiol, thereby causing an increase of the estradiol serum levels that is proportional to the amount of estradiol administered.

In another aspect, the present invention relates to an estradiol solution, as specified herein, for treating, alleviating, relieving, or preventing a physical condition in a female subject caused by deficient (insufficient) endogenous blood levels of estradiol, such as headaches, nausea, depression, vasomotor symptoms (hot flushes), symptoms of urogenital atrophy, loss of libido, decrease in bone mineral density, osteoporosis or increased risk or incidence of bone fractures.

In a preferred embodiment of the invention, the female subject to be treated is a woman with a deficient (too low)

level of estradiol, which is common during the menopause and postmenopause. In women in the reproductive age, normal estradiol levels range from 100-500 pg/ml during different parts of the menstrual cycle. In early menopause, estradiol levels are lower than 100 pg/ml and in late menopause decrease to 10-20 pg/ml. Value ranges of normal estradiol levels under 100 pg/ml can be associated with hot flushes, and may signal menopause. Menopause is the end of menstruation, which results from a reduced production of estrogen. During the menopause the number of follicles falls below a certain threshold, the ovaries can no longer produce mature follicles and sex hormones. As a consequence the ability to reproduce ends with menopause. The average age at which women go through the menopause is about 45-50 years. Because life expectancy is getting longer, women can now expect to be for a large part of their lives in the post-menopausal stage.

In a further embodiment of the invention, the female subject to be treated with the estradiol solution according to the invention is a hysterectomised woman. After total hysterectomy with removal of both ovaries, hormone production of estrogens (estradiol) and progestogens (progesterone) stops completely.

In women with an intact endometrium the use of estradiol monotherapy stimulates the proliferation of the endometrium. It is important to realize that also the opposing effect of progesterone, which terminates the proliferation of the endometrium, is absent in postmenopausal women. Since hyperplasia of the endometrium is a risk factor in the development of endometrial cancer, the endometrium of women on estradiol monotherapy should be protected by co-administering a progestogen, continuously or in a cyclic dosage regimen.

It may therefore be advantageous to use a progesterone solution for oromucosal co-administration in postmenopausal women in combination with the estradiol solutions of the present invention. Such progesterone solution can for instance be a solution containing 0.1-5% (w/v) progesterone in a solvent comprising 10-30% (qv) of a $C_2$-$C_5$ alcohol and 70-90% (v/v) of an ester of a $C_2$-$C_6$ alcohol and a $C_8$-$C_{22}$ fatty acid, e.g. a solution of ethanol and isopropyl myristate. In particular embodiments, said solution contains 0.5-4% (w/v), or 1-3% (w/v) progesterone.

Serum progesterone levels from 5 to 30 ng/ml (15-90 nmol/L) are considered representative of luteal phase progesterone levels, but also levels of 2-20 ng/ml (6-60 nmol/L) can be found in the literature. No specific levels needed to provide an adequate endometrial protection to estrogen replacement therapy in postmenopausal women are known, but are expected to be approximately 2 ng/ml and higher.

In a further aspect, the invention provides a formulation in the form of a solution as described herein, comprising a non-aqueous solution of progesterone in a concentration of 0.1-5% for oromucosal administration. By administration of a predetermined quantity of said solution, by a single or multiple administration, at one or more points in time, said quantity, representing a dose of 0.1-3 mg of progesterone, it is possible to obtain an increase of the progesterone serum levels that is proportional to the amount of progesterone administered. The increase in progesterone serum level may be approximately 0.3-2 ng/ml per 0.1 mg progesterone (or approximately 1-6 nmol/L per 0.1 mg progesterone).

Embodiments of this invention concern for instance 1.5% (w/v) progesterone oromucosal solutions comprising 150 mg progesterone, 3.0 ml ethanol, and 7.0 ml isopropyl myristate. 100 µl of such solutions represents 1.5 mg of progesterone, 50 µl represents 0.75 mg, while 25 µl represents 0.375 mg progesterone.

Other embodiments concern liquid solutions containing progesterone dissolved in solvents comprising ethanol and/or other $C_2$-$C_5$ alcohols and esters of isopropyl alcohol and/or other $C_2$-$C_6$ alcohols and $C_8$-$C_{22}$ fatty acids.

Such formulations can be administered independently from the estradiol administration, or at the same time.

Compositions in the form of a solution containing both estradiol and progesterone may be useful products for treating postmenopausal women with an intact endometrium and such compositions may also be useful contraceptive products.

Hence, in a further aspect, there is provided a non-aqueous (or substantially non-aqueous) solution containing 0.01-0.9% (w/v) of estradiol, or an equivalent amount of a pharmaceutically acceptable hydrate, or ester thereof, and 0.1 to 5% (w/v) of progesterone, 10-30% (v/v) or 5-40% (v/v) of a $C_2$-$C_5$ alcohol, and 70-90% (v/v) or 60-95% (v/v) of an ester of a $C_2$-$C_6$ alcohol and a $C_8$-$C_{22}$ fatty acid, for the treatment of a female with reduced estradiol levels, or for the manufacture of a medicament for the treatment of a female with reduced estradiol levels, by oromucosal administration of a dose of said solution, said dose containing 0.01-0.3 mg of estradiol or an equivalent amount of a pharmaceutically acceptable hydrate, or an ester thereof, and also containing 0.1-3 mg of progesterone, by single or multiple administration, at one or more points in time.

Another aspect concerns a non-aqueous (or substantially non-aqueous) solution containing 0.01-0.9% (w/v) of estradiol, or an equivalent amount of a pharmaceutically acceptable hydrate, or ester thereof, and 0.1 to 5% (w/v) of progesterone, 10-30% (v/v) of a $C_2$-$C_5$ alcohol, and 70-90% (v/v) of an ester of a $C_2$-$C_6$ alcohol and a $C_8$-$C_{22}$ fatty acid.

One embodiment concerns a non-aqueous (or substantially non-aqueous) solution containing 0.01-0.9% (w/v) of estradiol, or an equivalent amount of a pharmaceutically acceptable hydrate, or ester thereof, and 0.1 to 5% (w/v) of progesterone, 10-30% (v/v) of ethanol, and 70-90% (v/v) of isopropyl myristate.

The invention also concerns a product comprising or containing a solution of estradiol, as specified herein, and a solution of progesterone, as described herein, as a combined preparation for simultaneous, separate or sequential use for the treatment of a female with reduced estradiol levels.

The solutions of the present invention are superior in enhancing the oromucosal absorption of estradiol. The present invention consists of a solution that is completely water-free, contains ethanol en isopropyl myristate (or palmitate), and these components all contribute to the oromucosal absorption efficiency and total bioavailability of estradiol being surprisingly twice as good as the oromucosal Aerodiol™ administration.

The invention is illustrated by the following, non-limiting, examples.

EXAMPLES

Example 1

Estradiol Spray 0.3%

Estradiol 30 mg
Ethanol 2 ml
Isopropyl Myristate 8 ml
100 µl=300 µg
50 µl=150 µg
25 µl=75 µg

Example 2

Estradiol Spray 0.2%

Estradiol 20 mg
Ethanol 1.5 ml
Isopropyl Myristate 8.5 ml
100 µl=200 µg
50 µl=100 µg
25 µl=50 µg

Example 3

Estradiol Spray 0.1%

Estradiol 10 mg
Ethanol 1 ml
Isopropyl Palmitate 9 ml
100 µl=100 µg
50 µl=50 µg
25 µl=25 µg

Example 4

Estradiol Spray 0.05%

Estradiol 5 mg
Ethanol 2 ml
Isopropyl Palmitate 8 ml
100 µl=50 µg
50 µl=25 µg
20 µl=10 µg

Example 5

Estradiol Spray 0.4%

Estradiol 40 mg
Ethanol 1.5 ml
Isopropyl Myristate 8.5 ml
100 µl=400 µg
50 µl=200 µg
25 µl=100 µg

Example 6

Estradiol Levels Upon Administration of Solutions of the Invention

Ranges of normal estradiol levels are expressed in ng/l or pg/ml of estradiol (272 ng/l=272 pg/ml=1 nmol/l).

In women in the reproductive age, normal estradiol levels range from 100-500 pg/ml during different parts of the menstrual cycle.

In early menopause, estradiol levels are lower than 100 pg/ml and in late menopause decrease to 10-20 pg/ml. Value ranges of normal estradiol levels under 100 pg/ml can be associated with hot flushes, and may signal menopause.

These experiments were carried out in individual cases in postmenopausal women. Serum levels of estradiol were measured 30 minutes (between 25-35 minutes) after administering several doses of estradiol (by administering the buccal sprays described in examples 1 and 3). Results:

| Estradiol-dose | Formulation | Estradiol level | Increase per 10 µg |
|---|---|---|---|
| 25 µg | (example 3) | 101 pg/ml | 40 pg/ml |
| 150 µg | (example 1) | 715 pg/ml | 48 pg/ml |
| 75 µg | (example 1) | 339 pg/ml | 45 pg/ml |
| 150 µg | (example 1) | 704 pg/ml | 47 pg/ml |
| 100 µg | (example 3) | 412 pg/ml | 41 pg/ml |
| 75 µg | (example 3) | 302 pg/ml | 40 pg/ml |

The increase of the estradiol serum level per 10 µg estradiol dose was found to vary between about 40-50 pg/ml. For instance the increase is about 700 pg/ml per 150 µg estradiol dose.

These levels were compared with the levels from the literature achieved with nasal Aerodiol™, which is an aqueous solution of an estradiol-cyclodextrin complex. The mean peak serum level (Cmax) obtained with Aerodiol™ is approximately 1400 pg/ml after a dose of 300 µg estradiol, given as 2 nasal sprays of 150 µg (one in each nostril), and this level is between 600-800 pg/ml after a single nasal spray of 150 µg estradiol (Devissaguet et al. Eur. J. Drug Metabol. Pharmacokinetics 1999; 24:265-271).

Serum estradiol levels obtained after oromucosal administration of the present invention solutions are very similar, indicating that the estradiol amount absorbed from the oromucosal spray in the oral cavity is similar to the amounts of estradiol absorbed in the nose upon nasal administration of the product Aerodiol™.

However, the published product characteristics of Aerodiol™ disclose, that when Aerodiol™ is taken (in women with a blocked nose) by the oromucosal route, the estradiol absorption, and thus the Cmax and AUC are reduced to 50%. Women with a blocked nose have to take a double amount of the Aerodiol™ spray. This means that the estradiol from the solutions of the present invention is absorbed via the oromucosal route twice as good, which is a surprising result (Table 1).

TABLE 1

Comparison of AUC and Cmax using a similar dose of estradiol

| FORMULATION | AUC | Cmax |
|---|---|---|
| Aerodiol ™ taken as nasal spray (aqueous) | 100% | 100% |
| Aerodiol ™ taken as oromucosal spray (aqueous) | 50% | 50% |
| Estradiol oromucosal spray (present invention, non-aqueous) | 100% | 100% |

In other experiments 4 postmenopausal women received as a buccal spray 2×25 µl estradiol 0.2% (example 2), representing a dose of 100 µg estradiol. Serum levels of estradiol during 3 hours were as follows (Table 2):

TABLE 2

| Time in minutes | Mean estradiol level in pg/ml | Standard Deviation (SD) in pg/ml |
|---|---|---|
| 0 | 45 | (40) |
| 10 | 285 | (85) |
| 15 | 416 | (114) |
| 30 | 483 | (98) |
| 40 | 468 | (61) |
| 60 | 364 | (48) |
| 90 | 275 | (46) |
| 120 | 172 | (38) |
| 180 | 120 | (32) |

CONCLUSIONS

The results show that the mean estradiol level remains above 100 pg/ml for more than 3 hours, indicating that a dosage regimen comprising a dose of 100 μg estradiol administered oromucosally, using a spray bottle containing the present invention solution (example 2), is protecting women for more than 3 hours from hot flushes, which are associated with levels under 100 pg/ml. This protection would be even longer if the hot flushes are associated with estradiol levels under 50 pg/ml.

Further, when a oromucosal dose of 100 μg estradiol would have been given 2-4 times a day, with a dosing interval of 3-4 hours, for most of the day, women would be protected from hot flushes, associated with estradiol levels under 50 or 100 pg/ml.

The results also provide evidence, that the AUC (Area Under the Curve of the serum levels) measured after two, three or four estradiol oromucosal administrations of respectively 150 μg, 100 μg and 75 μg is approximately similar to the total AUC after nasal estradiol application of 300 μg nasal estradiol (Aerodiol™). This indicates that the oromucosal estradiol spray described in the present invention is bioequivalent to the nasal Aerodiol™ product that has been approved by the regulatory authorities in Europe in 2001.

The invention claimed is:

1. A method of treatment of a human female subject having reduced estradiol levels, said method consisting of administering oromucosally to the subject in need thereof one or more doses of a solution consisting of 0.01-0.9% (w/v) of estradiol, or an equivalent amount of a pharmaceutically acceptable hydrate or ester thereof, 5-30% (v/v) ethanol and 70-95% (v/v) of an ester of a $C_{2-6}$ alcohol and a $C_{8-22}$ fatty acid; wherein said dose comprises 0.01-0.3 mg of estradiol, or an equivalent amount of a pharmaceutically acceptable hydrate or ester thereof, and wherein the solution is administered 1-6 times per day by spray, by drops or by a dosage pen.

2. The method according to claim 1, wherein a volume between about 10-500 μl of the estradiol solution is administered per dose.

3. The method according to claim 1, wherein said dose is administered intermittently in a time period in the range 1 to 4 hours.

4. The method according to claim 1, wherein said treatment relieves—one or more symptoms secondary to the reduced estradiol levels in the subject, and said one or more symptoms is selected from the group consisting of headaches, nausea, vasomotor symptoms (hot flushes), symptoms of urogenital atrophy, decrease in bone mineral density, osteoporosis and increased risk or incidence of bone fractures.

5. The method of claim 1, wherein the solution contains 10-30% (v/v) ethanol and 70-90% (v/v) of said ester.

6. The method of claim 1, wherein the ester of the $C_{8-22}$ fatty acid and $C_{2-6}$ alcohol is a vegetable oil.

7. The method of claim 1, wherein the ester of the $C_{8-22}$ fatty acid and $C_{2-6}$ alcohol is isopropyl myristate or isopropyl palmitate.

8. The method of claim 1, wherein the solution contains 0.01-0.9% estradiol (w/v), 10-30% ethanol (v/v), and 70-90% (v/v) isopropyl myristate.

* * * * *